United States Patent [19]

Yoshizawa et al.

[11] Patent Number: 5,310,614

[45] Date of Patent: May 10, 1994

[54] ELECTROPHOTOGRAPHIC PHOTORECEPTOR HAVING AN ORGANIC PHOTOELECTROCONDUCTIVE LIGHT SENSITIVE LAYER

[75] Inventors: Hideo Yoshizawa; Kiyoshi Tamaki, both of Hachioji; Hajime Tadokoro, Hino; Yoshihide Fujimaki, Hachioji, all of Japan

[73] Assignee: Konica Corporation, Tokyo, Japan

[21] Appl. No.: 973,272

[22] Filed: Nov. 9, 1992

[30] Foreign Application Priority Data

Nov. 21, 1991 [JP] Japan .................................. 3-306355
Dec. 27, 1991 [JP] Japan .................................. 3-346868

[51] Int. Cl.⁵ .............................................. G03G 5/06
[52] U.S. Cl. .......................................... 430/59; 430/83
[58] Field of Search ............................ 430/59, 66, 83

[56] References Cited

U.S. PATENT DOCUMENTS 3,844,782  8/1974  Riester et al. ....................... 430/83
4,389,475  6/1983  Hoffmann et al. .................. 430/59
5,028,506  7/1991  Yamazaki et al. ................... 430/83

*Primary Examiner*—John Goodrow
*Attorney, Agent, or Firm*—Finnegan, Henderson, Farabow, Garrett & Dunner

[57] ABSTRACT

An electrophotographic photoreceptor is disclosed. The photoreceptor comprises a conductive support and a photosensitive layer provided thereon. The photosensitive layer contains a carrier generation material and a compound represented by the following formula 1, 2 or 3;

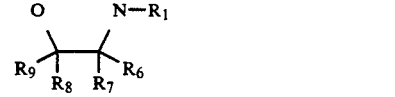

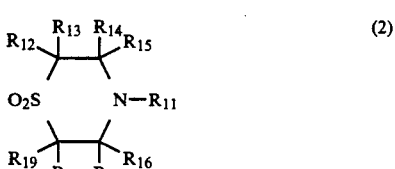

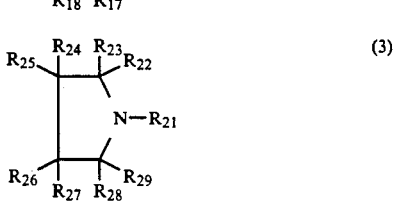

wherein $R_1$, $R_{11}$ and $R_{21}$ are each a hydrogen atom, an alkyl group, an alkoxy group, a cycloalkyl group, an alkenyl group, an aryl group, and aryloxy group or a heterocylic group; $R_2$ to $R_9$, $R_{12}$ to $R_{19}$ and $R_{22}$ to $R_{29}$ are independently a hydrogen atom, a halogen atom, an alkyl group, an alkoxy group, a cycloalkyl group, an aryl group or a heterocyclic group, said groups represented by $R_1$ to $R_9$, $R_{11}$ to $R_{19}$ and $R_{21}$ to $R_{29}$ each may have a substituent selected form a halogen atom, an alkyl group, an alkoxy group, an aryl group, an aryloxy group, a thioether group, an acyl group and sulfonamido group.

7 Claims, 1 Drawing Sheet

ELECTROPHOTOGRAPHIC PHOTORECEPTOR HAVING AN ORGANIC PHOTOELECTROCONDUCTIVE LIGHT SENSITIVE LAYER

FIELD OF THE INVENTION

The present invention relates to an electrophotographic photoreceptor, more specifically to an electrophotographic photoreceptor having an organic photoelectroconductive light-sensitive layer.

BACKGROUND OF THE INVENTION

In electrophotographic copying machines based on Carlson's method, charging the surface of a photoreceptor is followed by exposure to form an electrostatic latent image, which is developed with a toner, and the resulting visible image is transferred and fixed onto a transferee such as paper. At the same time, the photoreceptor is treated to remove the adhering toner, eliminate the charge and clean the surface to ensure long-term repeated use.

Therefore, the electrophotographic photoreceptor is required to have good physical properties such as printability, wear resistance and moisture resistance after repeated use and resistance to ozone generated upon corona discharge and to ultraviolet rays generated upon exposure (environmental resistance), as well as charging property and electrophotographic properties such as high sensitivity and low dark decay.

Conventional electrophotographic photoreceptors in common use are inorganic photoreceptors having a light-sensitive layer based mainly on an inorganic photoelectroconductive material such as selenium, zinc oxide or cadmium sulfide.

Meantime, the use of various organic photoelectroconductive materials for the light-sensitive layer of electrophotographic photoreceptor has recently been the subject of active R & D activities.

With respect to property requirements, the same applies to organic photoelectroconductive photoreceptors as for inorganic photoreceptors. For example, Japanese Patent Publication Open to Public Inspection (hereinafter referred to as Japanese Patent O.P.I. Publication) Nos. 71856/1988 and 71857/1988 propose the addition of particular compounds to improve performance.

However, improvements in potential stability and photoreceptor durability after repeated copying still remain unsatisfactory, requiring further improvement.

For example, Japanese Patent O.P.I. Publication Nos. 71855/1988, 71857/1988, 52150/1988, 50848/1988, 50849/1988, 50850/1988 and 50851/1988 propose the use of some additives for improving durability. These proposals aim mainly at prevention of photoreceptor performance degradation due to ozone generated upon charging. It should be noted, however, that photoreceptor durability degradation is caused not only by ozonic oxidation but also by repeated migration of electrons and holes in the light-sensitive layer and by NOx and SOx; in addition to ozonic oxidation, chargeability decreases and residual potential rises in repeated use.

A means or additive solving all these problems is demanded.

SUMMARY OF THE INVENTION

The object of the present invention is to provide an electrophotographic photoreceptor having an organic photoelectroconductive light-sensitive layer with high sensitivity and good durability.

The object of the invention described above is accomplished by an electrophotographic photoreceptor comprising an electroconductive support and a light-sensitive layer containing a carrier generation material (CGM) formed thereon, wherein at least one of the compounds represented by the following formulas 1, 2 and 3 is contained.

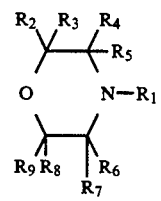

Formula 1 wherein $R_1$ represents a hydrogen atom, an alkyl group, an alkoxy group, a cycloalkyl group, an aryl group, an aryloxy group or a heterocyclic group, in which an aryl group and an alkyl group, particularly an aryl group, are preferable, $R_2$ through $R_9$ independently represent a hydrogen atom, a halogen atom, an alkyl group, an alkoxy group, a cycloalkyl group, an aryl group or an aryloxy group, in which an alkyl group and an alkoxy group are preferable. The above groups represented by $R_1$ through $R_9$ may have a substituent. Example of the substituents of the groups of $R_1$ through $R_9$ include halogen atoms, alkyl groups, alkoxy groups, aryl groups, aryloxy groups, thioether groups, acyl groups and sulfonamide groups.

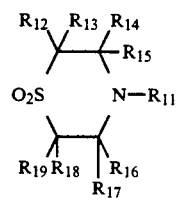

Formula 2 wherein $R_{11}$ represents a hydrogen atom, an alkyl group, an alkoxy group, a cycloalkyl group, an alkenyl group, an aryl group, an aryloxy group or a heterocyclic group, in which an aryl group and alkyl group, particularly an aryl group, are preferable, $R_{12}$ through $R_{19}$ independently represent a hydrogen atom, a halogen atom, an alkyl group, an alkoxy group, a cycloalkyl group, an aryl group or an aryloxy group, in which an alkyl group and alkoxy group are preferable. The above groups represented by $R_{11}$ through $R_{16}$ may have a substituent. Example of the substituents the groups represented by $R_{11}$ through $R_{19}$ include halogen atoms, alkyl groups, alkoxy groups, aryl groups, aryloxy groups, thioether groups, acyl groups and sulfonamide groups.

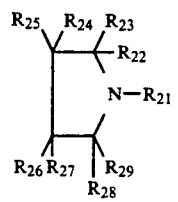

Formula 3 wherein $R_{21}$ represents a hydrogen atom, an alkyl group, an alkoxy group, a cycloalkyl group, an alkenyl group, an aryl group, an aryloxy group or a heterocyclic group, in which an aryl group and an alkyl group, particularly an aryl group, are preferable, $R_{22}$ through $R_{29}$ independently represent a hydrogen atom, a halogen atom, an alkyl group, an alkoxy group, a cycloalkyl group, an aryl group or an aryloxy group, in which an alkyl group and an alkoxy group are preferable. The above groups represented by $R_{21}$ through $R_{29}$ may have a substituent. Example of the substituents of the groups represented by $R_{21}$ through $R_{29}$ include halogen atoms, alkyl groups, alkenyl groups, alkoxy groups, aryl groups, aryloxy groups, thioether groups, acyl groups and sulfonamide groups.

DETAILED DESCRIPTION OF THE INVENTION

Figure 1:
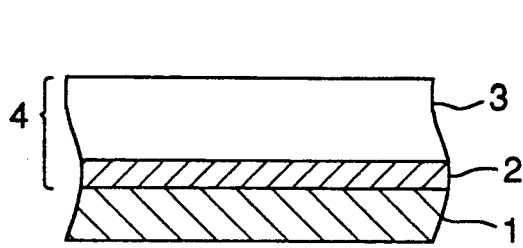
FIGS. 1 to 6 are cross-section showing mechanical configurations of photoreceptor of the invention.

The compounds represented by formulas 1 and 3 can easily be synthesized by known methods.

Example compounds are given below.

Example compounds represented by formula 1:

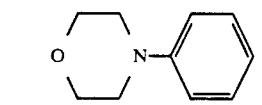
(1)-1

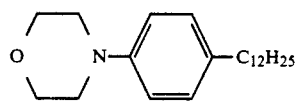
(1)-2

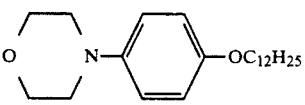
(1)-3

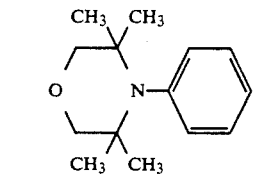
(1)-4

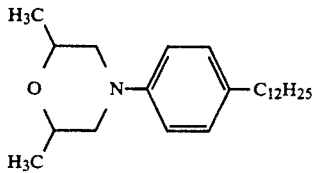
(1)-5

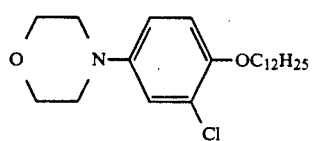
(1)-6

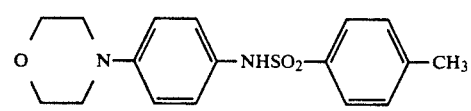
(1)-7

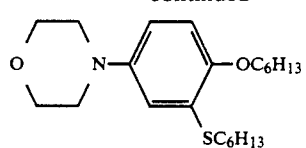
(1)-8

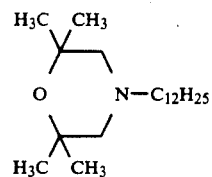
(1)-9

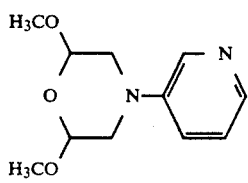
(1)-10

Example compounds represented by formula 2:

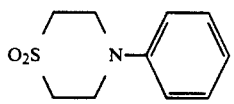
(2)-1

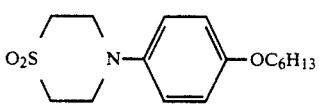
(2)-2

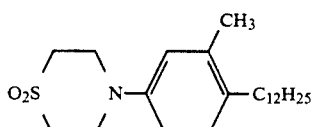
(2)-3

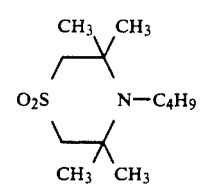
(2)-4

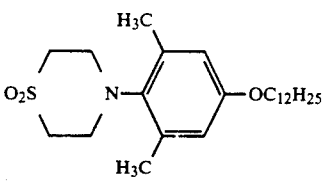
(2)-5

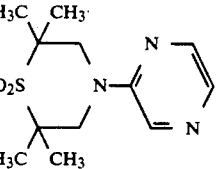
(2)-6

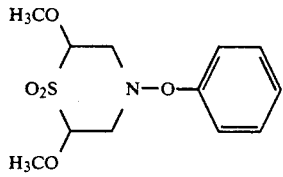
(2)-7

-continued

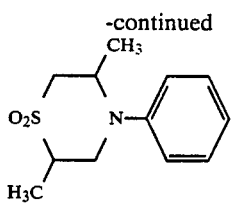

(2)-8

Example compounds represented by formula 3:

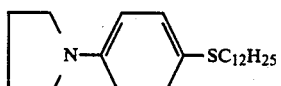 (3)-1

 (3)-2

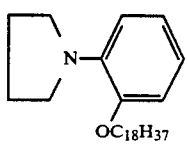 (3)-3

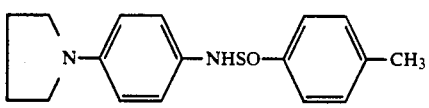 (3)-4

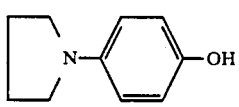 (3)-5

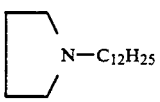 (3)-6

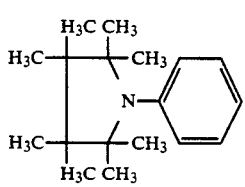 (3)-7

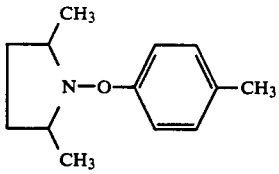 (3)-8

Preferably, the compound relating to the present invention is contained at 0.01 to 30% by weight of the total composition of the light-sensitive layer.

In the case that the carrier generation layer (CGL) and the carrier transport layer (CTL) are separately provided, when the compound is contained in the CGL, the amount of it is 0.01 to 30% by weight of the total composition of the CGL and when the compound is contained in the CTL, the amount of it is 0.01 to 30% by weight of the total composition of the CTL.

Compounds such as those described in Japanese Patent O.P.I. Publication Nos. 71857/1988, 13124/1990 and 37763/1992 are used as carrier generation materials (CGM) or carrier transport materials (CTM) in the present invention.

For example, organic pigments exemplified by the following are used as CGM.

(1) Azo pigments such as monoazo pigments, bisazo pigments, triazo pigments and metal complex salt azo pigments (2) Perillene pigments such as perillic anhydride and perillic imide.

(3) Polycyclic quinone pigments such as anthraquinone derivatives, anthanthrone derivatives, dibenzopyrenequinone derivatives, pyranthrone derivatives, violanthrone derivatives and isoviolanthrone derivatives.

(4) Indigoid pigments such as indigo derivatives and thioindigo derivatives.

(5) Phthalocyanine pigments such as metallic phthalocyanines and non-metallic phthalocyanines.

It is preferable to use an organic pigment such as a fluorenone dis-azo pigment, a fluorenylidene dis-azo pigment, a polycyclic quinone pigment, a non-metallic phthalocyanine pigment or an oxytitanyl phthalocyanine pigment as CGM in the electrophotographic photoreceptor of the present invention. When using a fluorenone dis-azo pigment, a fluorenylidene disazo pigment, a polycyclic quinone pigment, an X- or τ-type non-metallic phthalocyanine or the oxytitanyl phthalocyanine pigment described in Japanese Patent O.P.I. Publication No. 17066/1989 in the present invention, marked improvements are obtained in sensitivity, durability, image quality, etc.

There is no limitation on the choice of CTM for the present invention. Examples of usable CTMs include oxazole derivatives, oxadiazole derivatives, thiazole derivatives, thiadiazole derivatives, triazole derivatives, imidazole derivatives, imidazolone derivatives, imidazolidine derivatives, bisimidazolidine derivatives, styryl compounds, hydrazone compounds, pyrazoline derivatives, amine derivatives, oxazolone derivatives, benzothiazole derivatives, benzimidazole derivatives, quinazoline derivatives, benzofuran derivatives, acridine derivatives, phenazine derivatives, aminostylbene derivatives, poly-N-vinylcarbazole, poly-1-vinylpyrene and poly-9-vinylanthracene.

The CTM for the present invention is preferably one which is highly capable of transporting the holes which result upon light irradiation to the support side and which is suitable for combined use with the organic pigment for the present invention.

Example binders for the present invention are given below.
(1) Polyester
(2) Methacrylic resin
(3) Acrylic resin
(4) Polyvinyl chloride
(5) Polyvinylidene chloride
(6) Polystyrene
(7) Polyvinyl acetate
(8) Styrene copolymer resins such as styrene-butadiene copolymer and styrene-methyl methacrylate copolymer
(9) Acrylonitrile copolymer resins such as vinylidene chloride-acrylonitrile copolymer
(10) Vinyl chloride-vinyl acetate copolymer
(11) Vinyl chloride-vinyl acetate-maleic anhydride copolymer
(12) Silicone resin
(13) Silicone-alkyd resin

(14) Phenol resins such as phenol-formaldehyde resin and cresol-formaldehyde resin
(15) Styrene-alkyd resin
(16) Poly-N-vinylcarbazole
(17) Polyvinyl butyral
(18) Polyvinyl formal
(19) Polyhydroxystyrene
(20) Polycarbonate resin These binders may be used singly or in a mixture of two or more kinds.

Example dispersants for organic pigments for the present invention include hydrocarbons such as hexane, benzene, toluene and xylene, halogenated hydrocarbons such as methylene chloride, methylene bromide, 1,2-dichloroethane, syntetrachloroethane, cis-1,2-dichloroethylene, 1,1,2trichloroethane, 1,1,1-trichloroethane, 1,2-dichloropropane, chloroform, bromoform and chlorobenzene, ketones such as acetone, methyl ethyl ketone and cyclohexanone, esters such as ethyl acetate and butyl acetate, alcohols and derivatives thereof such as methanol, ethanol, propanol, butanol, cyclohexanol, heptanol, ethylene glycol, methyl cellosolve, ethyl cellosolve, acetyl cellosolve, ethers or acetals such as tetrahydrofuran, 1,4-dioxane, furan and furfural, nitrogen compounds such amines and amides including pyridine, butylamine, diethylamine, ethylenediamine, isopropanolamine and N,N-dimethylformamide, fatty acids, phenols and sulfur or phosphorus compounds such as carbon disulfide and triethyl phosphate.

In the present invention, for improving sensitivity, reducing residual potential and mitigating fatigue after repeated use and other purposes, the light-sensitive layer may incorporate one or more electron accepting substances.

Examples of electron acceptors which can be used for these purposes include highly electrophilic compounds such as succinic anhydride, maleic anhydride, dibromomaleic anhydride, phthalic anhydride, tetrachlorophthalic anhydride, tetrabromophthalic anhydride, 3-nitrophthalic anhydride, 4nitrophthalic anhydride, pyromellitic anhydride, mellitic anhydride, tetracyanoethylene, tetracyanoquinodimethane, o-dinitrobenzene, m-dinitrobenzene, 1,3,5-trinitrobenzene, p-nitrobenzonitrile, picryl chloride, quinone chlorimide, chloranil, bromanil, dichlorodicyanoparabenzoquinone, anthraquinone, dinitroanthraquinone, 2,7-dinitrofluorenone, 2,4,7-trinitrofluorenone, 2,4,5,7-tetranitrofluorenone, 9-fluorenylidene [dicyanomethylenemalonodinitrile], polynitro-9-fluorenylidene [dicyanomethylenemalonodinitrile], picric acid, o-nitrobenzoic acid, p-nitrobenzoic acid, 3,5-dinitrobenzoic acid, pentafluorobenzoic acid, 5-nitrosalicylic acid, 3,5-dinitrosalicylic acid, phthalic acid, mellitic acid. The amount of electron acceptor added is 0.01 to 200 parts by weight, preferably 0.1 to 100 parts by weight per 100 parts by weight of the organic pigment used for the invention.

The ratio of electron acceptor added to such a light-sensitive layer is 0.01 to 100 parts by weight, preferably 0.1 to 50 parts by weight per 100 parts by weight of the total CTM composition.

The light-sensitive layer for the present invention may incorporate an organic amine to improve the carrier generation function of CGM, with preference given to a secondary amine. Such compounds are specified in Japanese Patent O.P.I. Publication Nos. 218447/1984 and 8160/1987.

The light-sensitive layer for the present invention may incorporate an antioxidant for the purpose of prevention of ozonic deterioration.

Typical examples of such antioxidants are given below, which are not to be construed as limitative.
Group I : Hindered phenols
Group II : p-phenylenediamines
Group III: Hydroquinones
Group IV : Organic sulfur compounds.
Group V : Organic phosphorus compounds These compounds are disclosed in Japanese Patent O.P.I. Publication No. 18354/1988, for instance.

These compounds, known as antioxidants for rubber, plastics, oils and fats, etc., are easily available on a commercial basis.

The amount of antioxidant added is 0.1 to 100 parts by weight, preferably 1 to 50 parts by weight, and more preferably 5 to 25 parts by weight per 100 parts by weight of CTM.

The photoreceptor of the present invention may incorporate as necessary an ultraviolet absorbent and other additives to protect the light-sensitive layer and also a color sensitivity correcting dye.

The protective layer relating to the present invention may incorporate when necessary a thermoplastic resin at concentrations of under 50% by weight for the purpose of improving workability and physical properties, for example, to prevent cracking and to provide flexibility.

The interlayer, which functions as an adhesive layer, blocking layer or other types of layers, may comprise, for example, polyvinyl alcohol, ethyl cellulose, carboxymethyl cellulose, vinyl chloride-vinyl acetate copolymer, vinyl chloride-vinyl acetate-maleic anhydride copolymer, casein, N-alkoxymethylated nylon, starch as well as the above-mentioned binder resins.

The electroconductive support which constitutes the electrophotographic photoreceptor of the present invention is prepared mainly from the following substances, which are not to be construed as limitative.
1) Metal plates such as aluminum and stainless steel plates.
2) Paper or plastic film supports having a thin layer of a metal such as aluminum, palladium or gold formed thereon by lamination or evaporative deposition.
3) Paper or plastic film supports having a layer of an electroconductive compound such as an electroconductive polymer, indium oxide or tin oxide formed thereon by coating or evaporative deposition.

In the present invention, the composition, material, thickness and other factors of support, CGL, CTL, interlayer and overcoat layer can be set in accordance with the conditions described in Japanese Patent O.P.I. Publication Nos. 71857/1988, 155047/1988, 155048/1988, 155049/1988, 55050/1988 and 15505/1981, 302264/1989, 319043/1989, 131243/1990, 11358/1991, 96958/1991, 248159/1991 and 37764/1992.

Figure 2:
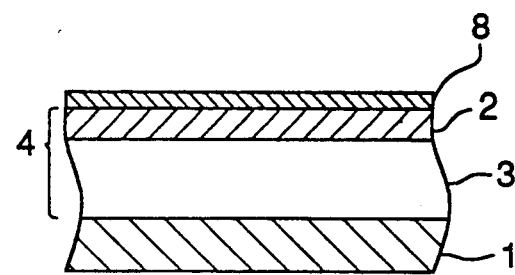
Figure 3:
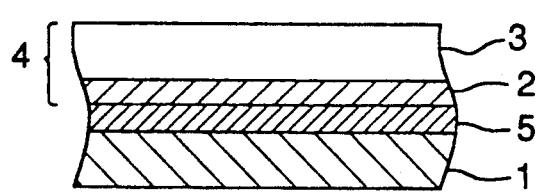
Figure 4:
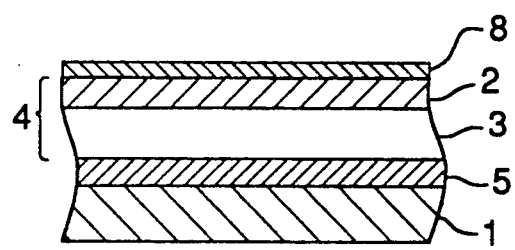

The photoreceptor of the present invention is prepared by forming a light-sensitive layer 4 on an electroconductive support 1, which light-sensitive layer comprises a lamination of CGM-based CGL 2 CTM-based CTL 3, as illustrated in FIG. 1 and FIG. 2. As illustrated in FIG. 3 and FIG. 4, the light-sensitive layer 4 may be formed via an interlayer 5 on electroconductive support 1. An electrophotographic photoreceptor with the most preferable electrophotographic properties is obtained when light-sensitive layer 4 is configured with two layers as above. In the present invention, light-sensitive layer 4 wherein fine particles of CGM 7 are dispersed in binder resin in a CTM-based layer 6 may be formed on electroconductive support 1 directly or via interlayer 5, as illustrated in FIG. 5 and FIG. 6.

Figure 5:
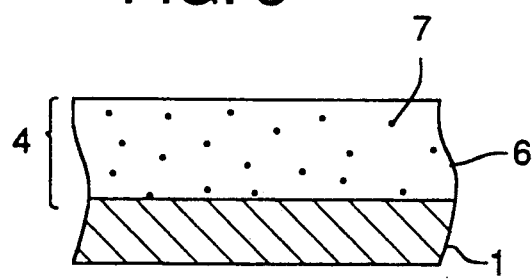
Figure 6:
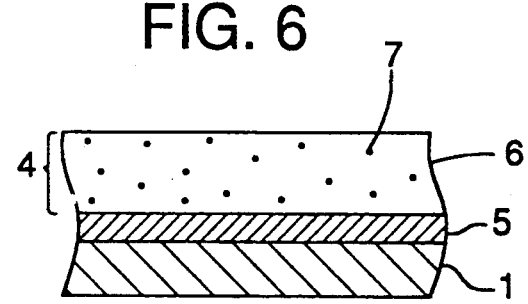

In the present invention, the light-sensitive layer may also be one wherein CGM 7 is dispersed in binder resin in the absence of CTM as shown in FIG. 5 and FIG. 6.

Also, CTM may be added to CGL, as long as the amount of its addition is not more than 300 parts by weight, preferably not more than 200 parts by weight per 100 parts by weight of CGM.

The light-sensitive layer 4 may be provided with a protective layer 8 thereon when necessary.

When light-sensitive layer 4 is of a double layer structure, whether CGL 2 or CTL 3 is the upper layer depends on charge polarity. To obtain a negatively charged light-sensitive layer, it is advantageous to position CTL 3 on CGL 2. This is because the CTM in CTL 3 is highly capable of transporting positive holes.

CGL 2 constituting double-layered light-sensitive layer 4 can be prepared on electroconductive support 1 or CTL 3 directly or via an adhesive layer, blocking layer or other types of interlayers formed when necessary as follows:

(1) Vacuum deposition.
(2) Coating a solution of CGM in an appropriate solvent.
(3) Coating a dispersion prepared by finely pulverizing a CGM in a dispersant using a ball mill, sand grinder or other means, and if necessary, mixing and dispersing with a binder.

Specifically, there can be used optionally vapor phase deposition methods such as vacuum deposition, sputtering and CVD and coating methods such as dip coating, spray coating, blade coating and roll coating.

The thickness of CGL 2 thus formed is preferably 0.01 to 10 μm, more preferably 0.05 to 5 μm.

The thickness of CTL 3, can be changed when necessary, is preferably 5 to 30 μm. The binder content in this CTL 3 is preferably 0.1 to 5 parts by weight of binder per 1 part by weight of CTM 1 for the present invention, but when forming light-sensitive layer 4 containing fine grains of CGM dispersed therein, it is preferable to use the binder in a ratio of not more than 5 parts by weight per 1 part by weight of CGM. When CGL is formed as a dispersion in binder, it is preferable to use the binder in a ratio of not more than 5 parts by weight per 1 part by weight of CGM.

EXAMPLES

Example 1

A solution of 3 parts by weight of copolymer nylon (CM-8000, produced by Toray Industries, Inc.), 90 parts by weight of methanol and 10 parts by weight of butanol was coated on an aluminum drum of 60 mm diameter for the KONICA laser printer LP-3115 to obtain an undercoating layer (UCL) of 0.3-μm thickness.

Next, 4 parts by weight of titanyl phthalocyanine TiOPc (described in Synthesis Example 1 of Japanese Patent O.P.I. Publication No. 131243/1990), as CGM, 20 parts by weight of silicone resin KR-5240 (produced by Shin-Etsu Chemical Co., Ltd.) and 100 parts by weight of methyl ethyl ketone were milled and dispersed using a sand grinder. This dispersion was coated on the undercoating layer by the dip coating method to form a 0.3 μm thick CGL.

Separately, 10 parts by weight of CTM, 15 parts by weight of polycarbonate resin Iupiron Z (produced by Mitsubishi Gas Chemical Co., Inc.), 0.001 part by weight of silicone oil KF-54 (produced by Shin-Etsu Chemical Co., Ltd.) and 0.1 part by weight of compound (1)-3 relating to the present invention were dissolved in 1,2-dichloroethane, and this solution was dip coated on the CGL and dried at 90° C. for 1 hour to form a 20-μm thick CTL. to obtain a photoreceptor.

Examples 2 through 10, 19 through 21 and Comparative Examples 1 and 5

Photoreceptors were prepared in the same manner as in Example 1 except that the binder in UCL, and the CGM, CTM and compounds in CGL and CTL were replaced as shown in Table 1.

Examples 22 through 24 and Comparative Example 6

A photoreceptor was prepared in the same manner as in Example 1 except that the relative vertical positions of CGL and CTL were reversed.

Examples 25 through 27

UCL was formed on the same 60-mm diameter aluminum drum for LP-3115 as above in the same manner as in Example 1, and 0.2 parts by weight of compound (1)-4 was added to CGL solution, followed by the same procedure as in Example 1 except that compound (1)-3 was not added to CTL solution to obtain a photoreceptor having a 0.3 μm CGL and a 20-μm CTL.

Examples 28 through 30 and Comparative Example 7

UCL was formed on a 60 mm diameter aluminum drum in the same manner as in Example 1, and 20 parts by weight of X-type non-metallic phthalocyanine, as pigment, and 5% by weight of compound (1)-5, (2)-6 or (3)-5, 40 parts by dry weight of polyester resin ALUMATEX P-645 (produced by Mitsui Toatsu Chemical, Inc.) and 10 parts by dry weight of melanin resin UVAN 21 (produced by Mitsui Toatsu Chemicals, Inc.), as binders, and 450 parts by weight of cyclohexane were mixed and dispersed in a sand grinder. The resulting dispersion was dip coated on the UCL and dried at 150° C. for 1 hour to obtain a single layered light-sensitive layer, 15 μm thick.

Example 11

A solution of 3 parts by weight of methoxy-modified nylon Diamide X-1874M (Daicel Chemical Industries, Ltd.), 90 parts by weight of methanol and 10 parts by weight of butanol was coated on a 80 mm diameter aluminum drum for the KONICA copying machine U-Bix 3035 to obtain a UCL, 0.3 μm thick.

Next, a dispersion obtained by mixing and dispersing 4 parts by weight of the following compound G3, 2 parts by weight of butyral resin S-LEC BL-1 (produced by Sekisui Chemical Co., Ltd.) and 100 parts by weight of methyl ethyl ketone was dip coated to obtain a CGL, 0.3 μm thick. On the CGL, a CTL was formed in the same manner as in Example 1 except that the compound for CTL solution in Example 1 was replaced with a compound of Table 2.

Examples 2 through 18 and Comparative Examples 2 through 4

Photoreceptors were prepared in the same manner as in Example 11 except that the binder for UCL, and the CGM, CTM and compounds for CGL and CTL were replaced as shown in Table 1.

G1: Titanyl phtalocyanine (TiOPc)
G2: X-type non-metallic phtalocyanine (X-H₂Pc)

T1:

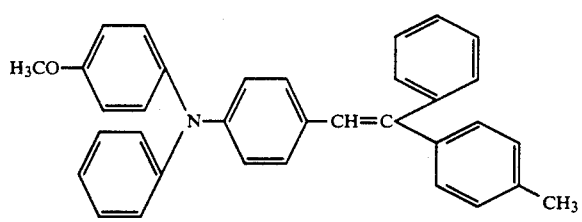

T2:

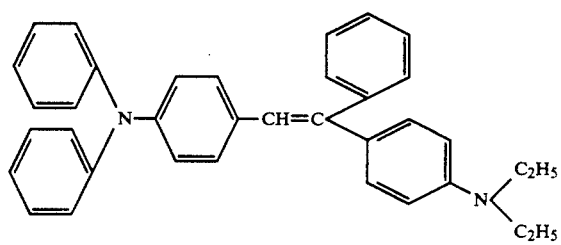

T3:

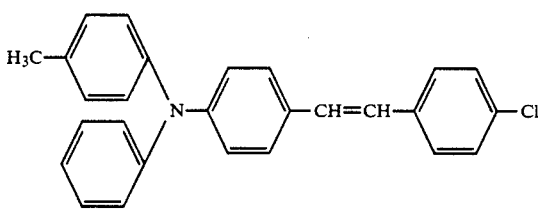

B3:
Modified nylon Diamide X-1874M
(produced by Daicel Chemical Industries, Ltd.)

G3:

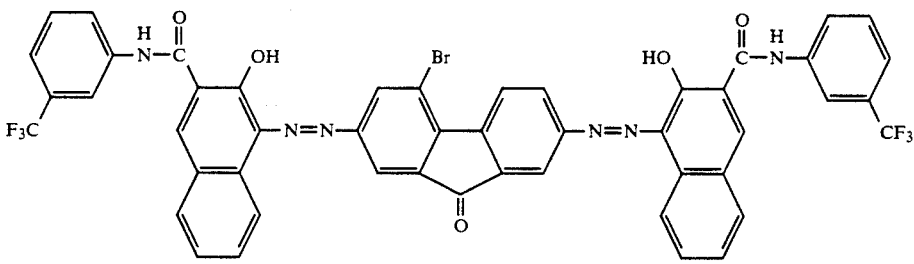

G4:

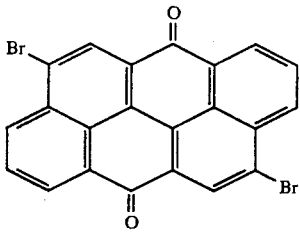

Examples 31 through 33

Examples 31, 32 and 33 were prepared in the same meanner as in Example 1, except that the compound of the invention is added to both of CGL and CTL thereof.

The binders B1, B2 and B3, CGMs G1 to G2, and G4 and CTMs T1, T2 and T3 of UCL used in Example are as follows.

B1: Copolymerized modified nylon (CM-8000, produced by Toray Industries, Inc.)
B2: Vinyl chloride-vinyl acetate-maleic anhydride copolymer (S-lec MF-10, Sekisui Chemical Co., Ltd.)

Evaluation of performance

Each of the samples obtained in Examples 1 through 10, 19 through 33 and Comparative Examples 1 and 5 through 7 was used on a modification of the KONICA laser printer LP-3115 to take multiple copies, and the potential $V_L$ in the exposed portion was measured and the potential $V_H$ in the unexposed portion and image quality were evaluated after 10000 copies were taken. The results are shown in Table 1. Each of the samples obtained in Examples 11 through 18 and Comparative Examples 2 through 4 was used on a modification of the KONICA U-Bix 3035 to take multiple copies, and the potential $V_H$ at an optical density OD of 1.3 and the potential $V_L$ at an OD of 0.08 and image quality were evaluated after 10000 copies were taken. The results are shown in Table 1.

TABLE 1

| | | CGL | | | CTL | | | Potential at the initial time | | Potential after 10000 copies | | Image quality after |
|---|---|---|---|---|---|---|---|---|---|---|---|---|
| Sample No. | UCL | CGM | Compound of formula 1, 2 or 3 | Adding amount (wt %) | CTM | Compound of formula 1, 2 or 3 | Adding amount (wt %) | VH | VL | VH | VL | 10000 copies |
| Example 1 | B1 | G1 | — | — | T1 | (1)-3 | 0.1 | −600 | −50 | −590 | −45 | good |
| Example 2 | B1 | G1 | — | — | T1 | (1)-2 | 1 | −600 | −50 | −590 | −50 | good |
| Example 3 | B1 | G1 | — | — | T1 | (1)-1 | 3 | −600 | −45 | −590 | −40 | good |
| Example 4 | B1 | G2 | — | — | T2 | (1)-4 | 7.5 | −600 | −65 | −590 | −65 | good |
| Example 5 | B1 | G1 | — | — | T1 | (2)-2 | 3 | −600 | −60 | −600 | −55 | good |
| Example 6 | B1 | G1 | — | — | T1 | (2)-4 | 0.5 | −600 | −50 | −600 | −50 | good |
| Example 7 | B1 | G1 | — | — | T1 | (2)-3 | 0.1 | −600 | −50 | −600 | −45 | good |
| Example 8 | B1 | G1 | — | — | T1 | (2)-8 | 0.2 | −600 | −50 | −600 | −50 | good |
| Example 9 | B1 | G2 | — | — | T2 | (2)-6 | 7.5 | −600 | −65 | −590 | −65 | good |
| Example 10 | B2 | G4 | — | — | T3 | (1)-8 | 1 | −600 | −70 | −600 | −65 | good |
| Example 11 | B3 | G3 | — | — | T1 | (1)-1 | 0.5 | −700 | −70 | −680 | −60 | good |
| Example 12 | B2 | G4 | — | — | T1 | (2)-2 | 0.05 | −700 | −95 | −690 | −90 | good |
| Example 13 | B3 | G3 | — | — | T1 | (2)-7 | 1 | −700 | −80 | −690 | −75 | good |
| Example 14 | B2 | G4 | — | — | T3 | (2)-3 | 1 | −700 | −70 | −690 | −65 | good |
| Example 15 | B2 | G3 | — | — | T2 | (3)-1 | 0.5 | −700 | −50 | −700 | −45 | good |
| Example 16 | B2 | G3 | — | — | T2 | (3)-2 | 0.1 | −700 | −55 | −700 | −50 | good |
| Example 17 | B2 | G4 | — | — | T2 | (3)-3 | 1 | −700 | −60 | −700 | −50 | good |
| Example 18 | B2 | G4 | — | — | T2 | (3)-4 | 1 | −700 | −70 | −690 | −70 | good |
| Example 19 | B1 | G1 | — | — | T1 | (3)-1 | 3 | −600 | −40 | −590 | −40 | good |
| Example 20 | B1 | G1 | — | — | T1 | (3)-6 | 7.5 | −600 | −45 | −590 | −40 | good |
| Example 21 | B1 | G1 | — | — | T1 | (3)-5 | 0.1 | −600 | −55 | −600 | −55 | good |
| Example 22 | B1 | G1 | — | — | T1 | (1)-3 | 0.1 | +600 | +70 | +590 | +50 | good |
| Example 23 | B1 | G1 | — | — | T1 | (2)-4 | 0.5 | +600 | +75 | +590 | +70 | good |
| Example 24 | B1 | G1 | — | — | T1 | (3)-3 | 1 | +600 | +70 | +590 | +70 | good |
| Example 25 | B1 | G1 | (1)-4 | 0.2 | T1 | — | — | −600 | −50 | −600 | −50 | good |
| Example 26 | B1 | G1 | (2)-2 | 0.2 | T1 | — | — | −600 | −55 | −600 | −50 | good |
| Example 27 | B1 | G1 | (3)-4 | 0.2 | T1 | — | — | −600 | −60 | −590 | −55 | good |
| Example 28 | B1 | G2 | (1)-5 | 5 | — | — | — | +600 | +30 | +590 | +30 | good |
| Example 29 | B1 | G2 | (2)-6 | 5 | — | — | — | +600 | +25 | +590 | +20 | good |
| Example 30 | B1 | G2 | (3)-5 | 5 | — | — | — | +600 | +25 | +590 | +20 | good |
| Example 31 | B1 | G1 | (1)-3 | 0.2 | T1 | (1)-3 | 0.1 | −600 | −55 | −590 | −50 | good |
| Example 32 | B1 | G1 | (2)-1 | 0.2 | T1 | (2)-1 | 0.3 | −600 | −50 | −590 | −50 | good |
| Example 33 | B1 | G1 | (3)-2 | 0.2 | T1 | (3)-2 | 0.3 | −600 | −50 | −590 | −45 | good |
| Comparative 1 | B1 | G1 | — | — | T1 | — | — | −600 | −50 | −520 | −30 | Fogging[1] |
| Comparative 2 | B2 | G3 | — | — | T2 | — | — | −700 | −90 | −620 | −80 | Density[2] decreasing |
| Comparative 3 | B1 | G3 | — | — | T2 | — | — | −700 | −50 | −610 | −50 | Fogging[1] |
| Comparative 4 | B2 | G4 | — | — | T2 | — | — | −700 | −60 | −620 | −50 | Density[2] decreasing |
| Comparative 5 | B2 | G2 | — | — | T2 | — | — | −600 | −50 | −520 | −65 | Density[2] decreasing |
| Comparative 6 | B1 | G1 | — | — | T1 | — | — | +600 | +75 | +500 | +65 | Fogging[1] |
| Comparative 7 | B1 | G2 | — | — | — | — | — | +600 | +30 | +430 | +30 | Fogging[1] |

[1] Fogging: Fog was formed on background.
[2] Density decreasing: Density of the image was lowered.

As seen in Table 3, the samples prepared in accordance with the present invention retained a good potential characteristic even after 10000 copies (prints) were taken, while the comparative sample had decreased $V_H$ and background fogging or image density deterioration.

What is claimed is:

1. An electrophotographic photoreceptor comprising a conductive substrate having thereon a photosensitive layer containing a carrier generation material and a compound represented by the following formula 1, 2 or 3;

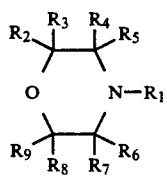
(1)

wherein $R_1$ is a hydrogen atom, an alkyl group, an alkoxy group, a cycloalkyl group, an aryl group, an aryloxy group or a heterocylic group; $R_2$, $R_3$, $R_4$, $R_5$, $R_6$, $R_7$, $R_8$ and $R_9$ are independently a hydrogen atom, a halogen atom, an alkyl group, an alkoxy group, a cycloalkyl group, an aryl group or an aryloxy group, said groups represented by $R_1$, $R_2$, $R_3$, $R_4$, $R_5$, $R_6$, $R_7$, $R_8$ and $R_9$ each may have a substituent selected from a halogen atom, an alkyl group, an alkoxy group, an aryl group, an aryloxy group, a thioether group, an acyl group and sulfonamido group,

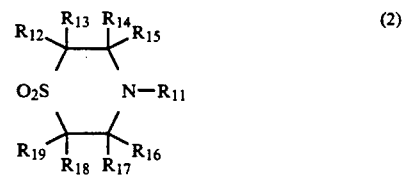
(2)

wherein $R_{11}$ l is a hydrogen atom, an alkyl group, an alkoxy group, a cycloalkyl group, an alkenyl group, an aryl group, an aryloxy group or a heterocyclic group; $R_{12}$, $R_{13}$, $R_{14}$, $R_{15}$, $R_{16}$, $R_{17}$, $R_{18}$ and $R_{19}$ are independently a hydrogen atom, a halogen atom, an alkyl group, an alkoxy group, a cycloalkyl group, an aryl group or an aryloxy group, said groups represented by $R_{11}, R_{12}, R_{13}, R_{14}, R_{15}, R_{16}, R_{17}, R_{18}$ and $R_{19}$ each may have a substituent selected from a halogen atom, an alkyl group, an alkoxy group, an aryl group, an aryloxy group, a thioether group, an acyl group and sulfonamido group,

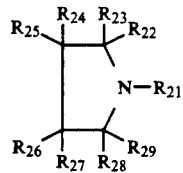
(3)

wherein $R_{21}$ is a hydrogen atom, an alkyl group, an alkoxy group, a cycloalkyl group, an alkenyl group, an aryl group, an aryloxy group or a heterocylic group; $R_{22}, R_{23}, R_{24}, R_{25}, R_{26}, R_{27}, R_{28}$ and $R_{29}$ are independently a hydrogen atom, a halogen atom, an alkyl group, an alkoxy group, a cycloalkyl group, an aryl group or an aryloxy group, said groups represented by $R_{21}, R_{22}, R_{23}, R_{24}, R_{25}, R_{26}, R_{27}, R_{28}$ and $R_{29}$ each may have a substituent selected from a halogen atom, an alkenyl group, an alkoxy group, an aryl group, an arylpxy group, a thioether group, an acyl group and sulfonamido group.

2. The photoreceptor of claim 1, wherein said photosensitive layer contains a carrier generation material and a compound represented by Formula 1.

3. The photoreceptor of claim 1, wherein said photosensitive layer contains a carrier generation material and a compound represented by Formula 2.

4. The photoreceptor of claim 1, wherein said photosensitive layer contains a carrier generation material and a compound represented by Formula 3.

5. The photoreceptor of claim 1, wherein said photosensitive layer contains said compound of formula 1, 2 or 3 in an amount of 0.01% to 30% by weight of the total weight of said photosensitive layer.

6. The photoreceptor of claim 1, wherein said photosensitive layer comprising said carrier generation layer and said compound of formula 1, 2 or 3 additionally comprises a carrier transport layer.

7. The photoreceptor of claim 6, wherein said carrier generation layer and said carrier trasport layer each contains said compound of formula 1, 2 or 3 in an amount of 0.01% to 30% by weight of the total weight of said carrier generation layer and said carrier transport layer, respectively.

* * * * *

UNITED STATES PATENT AND TRADEMARK OFFICE
CERTIFICATE OF CORRECTION

PATENT NO. : 5,310,614
DATED : May 10, 1994
INVENTOR(S) : Hideo Yoshizawa et al.

It is certified that error appears in the above-indentified patent and that said Letters Patent is hereby corrected as shown below:

Claim 1, column 14, line 63, delete "1".
        column 15, line 25: after "atom," insert --an alkyl group,--.
        column 16, line 1: "arylpxy" should read --aryloxy--.
Claim 7, column 16, line 21: "trasport" should read --transport--.

Signed and Sealed this

Fifteenth Day of November, 1994

Attest:

BRUCE LEHMAN

Attesting Officer      Commissioner of Patents and Trademarks